(12) United States Patent
Magendie et al.

(10) Patent No.: US 7,053,138 B2
(45) Date of Patent: May 30, 2006

(54) FLAME-PROOFING AGENTS

(75) Inventors: Franck Magendie, Huningue (FR); Ulrich Weidmann, Basel (CH)

(73) Assignee: Huntsman Advanced Materials Americas Inc., The Woodlands, TX (US)

( * ) Notice: Subject to any disclaimer, the term of this patent is extended or adjusted under 35 U.S.C. 154(b) by 245 days.

(21) Appl. No.: 10/466,944

(22) PCT Filed: Nov. 20, 2001

(86) PCT No.: PCT/EP01/13430

§ 371 (c)(1), (2), (4) Date: Jul. 21, 2003

(87) PCT Pub. No.: WO02/057279

PCT Pub. Date: Jul. 25, 2002

(65) Prior Publication Data
US 2004/0054120 A1    Mar. 18, 2004

(30) Foreign Application Priority Data
Jan. 22, 2001   (CH) .......................... 99/01

(51) Int. Cl.
C08L 63/00 (2006.01)
C07D 265/00 (2006.01)
C07D 413/02 (2006.01)
C07D 413/14 (2006.01)
C07F 9/28 (2006.01)

(52) U.S. Cl. ...................... 523/451; 523/456; 523/461; 544/63; 544/72; 544/73; 544/88; 544/89; 544/96; 562/11; 562/12; 562/19; 562/20; 562/23; 564/16

(58) Field of Classification Search .................... 544/1, 544/63, 72, 73, 88, 89, 96; 562/8, 11, 12, 562/19, 23, 24; 564/1, 15, 16; 523/400, 523/451, 456, 87, 88, 89, 93, 94, 104, 107, 523/708, 116, 117, 118, 119, 121, 124, 417, 523/418; 528/420, 421, 422, 423
See application file for complete search history.

(56) References Cited
OTHER PUBLICATIONS

JP 2002-138096: Hiroshi et al., published May 14, 2002.*
Machine translation of JP 2002-138096, provided by the JPO website.*

* cited by examiner

Primary Examiner—Michael J. Feely
(74) Attorney, Agent, or Firm—Robert Holthus

(57) ABSTRACT

Compounds of formula (I) or (II), wherein $R_1$ is $C_1$–$C_{18}$alkyl; $C_5$–$C_{12}$cycloalkyl that is unsubstituted or substituted by one or more $C_1$–$C_6$alkyl groups or $C_1$–$C_6$alkoxy groups; $C_5$–$C_{22}$aryl that is unsubstituted or substituted by one or more $C_1$–$C_6$alkyl groups or $C_1$–$C_6$alkoxy groups; or $C_7$–$C_{30}$aralkyl that is unsubstituted or substituted by one or more $C_1$–$C_6$alkyl groups or $C_1$–$C_6$alkoxy groups, and the radicals $R_2$ to $R_{13}$ are each independently of the others hydrogen; —$NO_2$; dialkylamino; alkylthio; alkylsulfonyl; halogen; $C_1$–$C_{18}$alkyl; $C_1$–$C_{18}$alkoxy; $C_1$–$C_{18}$alkoxyalkyl; $C_5$–$C_{12}$cycloalkyl that is unsubstituted or substituted by one or more $C_1$–$C_6$alkyl groups or $C_1$–$C_6$alkoxy groups; $C_5$–$C_{22}$aryl that is unsubstituted or substituted by one or more $C_1$–$C_6$alkyl groups or $C_1$–$C_6$alkoxy groups; or $C_7$–$C_{30}$aralkyl that is unsubstituted or substituted by one or more $C_1$–$C_6$alkyl groups or $C_1$–$C_6$alkoxy groups, are suitable as flame-proofing agents for thermoplastic or thermosetting polymers

27 Claims, No Drawings

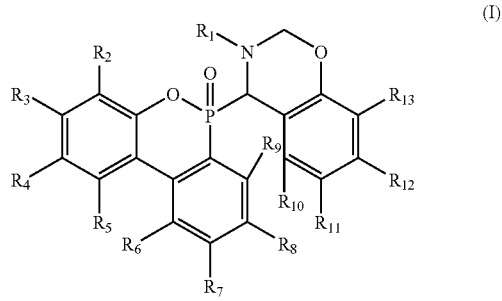

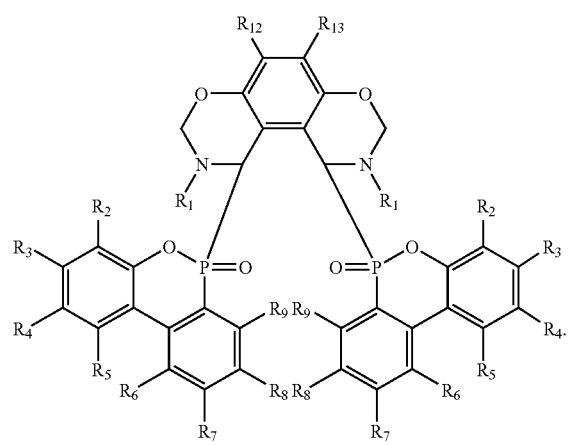

FLAME-PROOFING AGENTS

The present invention relates to novel benzoxazines, intermediates and a process for the preparation thereof, to compositions comprising such benzoxazines and to the use of such compositions in the manufacture of prepregs and laminates.

The use of halogen-containing flame-proofing agents in encapsulating and laminating resins is problematic owing to the toxicity of the combustion products and the corrosive action of the hydrogen halide released. Accordingly, for those applications greater use has been made recently of phosphorus-containing flame-proofing agents.

For example, resins having very good flame-resistance and a high glass transition temperature $T_g$ are obtained when glycidyl ethers are pre-lengthened with 2-(6-oxide-6H-dibenz-1,2-oxaphosphorin-6-yl)-1,4-dihydroxybenzene (C. -S. Wang, M. -C. Lee: "Synthesis and properties of epoxy resins containing 2-(6-oxide-6H-dibenz(c,e)(1,2) oxaphosphorin-6-yl) 1,4-benzenediol (II)", Polymer 41, 3631–3638 (2000)).

Similarly good results are obtained with phosphorus-containing epoxy resins prepared by the reaction of epoxy novolaks and 9,10-dihydro-9-oxa-10-phosphaphenanthrene-10-oxide (DOPO) (C. -S. Wang, C. -H. Lin: "Novel phosphorus-containing epoxy resins, Part II: Curing kinetics", Polymer 41, 8579–8586 (2000)).

In respect of important laminate properties, such as dielectric strength (pressure cooker test), those flame-proofed resins do not, however, meet all requirements.

It has now been found that the addition of relatively small amounts of a specific DOPO derivative to epoxy resins yields flame-proofed laminating resins that have high glass transition temperatures and also yield good results in the pressure cooker test.

The present invention relates to a compound of formula I or II

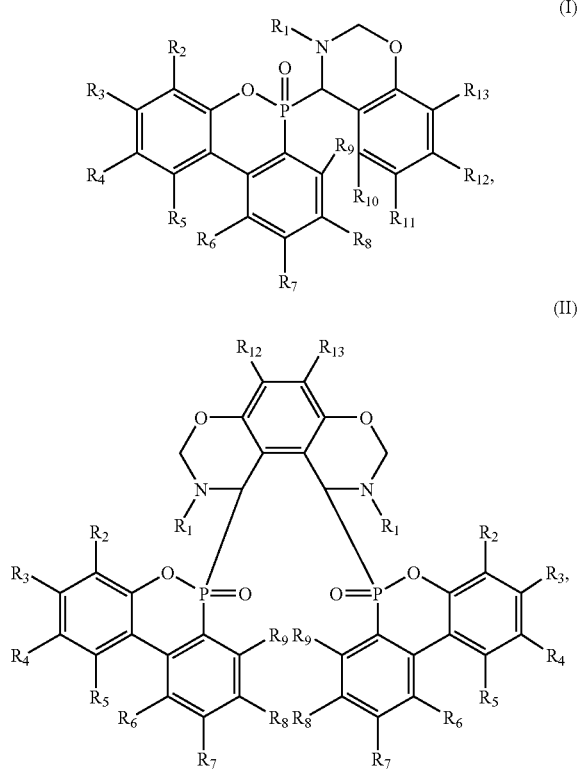

wherein $R_1$ is $C_1–C_{18}$alkyl; $C_5–C_{12}$cycloalkyl that is unsubstituted or substituted by one or more $C_1–C_6$alkyl groups or $C_1–C_6$alkoxy groups; $C_5–C_{22}$aryl that is unsubstituted or substituted by one or more $C_1–C_6$alkyl groups or $C_1–C_6$alkoxy groups; or $C_7–C_{30}$aralkyl that is unsubstituted or substituted by one or more $C_1–C_6$alkyl groups or $C_1–C_6$alkoxy groups, and the radicals $R_2$ to $R_{13}$ are each independently of the others hydrogen; —$NO_2$; dialkylamino; alkylthio; alkylsulfonyl; halogen; $C_1–C_{18}$alkyl; $C_1–C_{18}$alkoxy; $C_1–C_{18}$alkoxyalkyl; $C_5–C_{12}$cycloalkyl that is unsubstituted or substituted by one or more $C_1–C_6$alkyl groups or $C_1–C_6$alkoxy groups; $C_5–C_{22}$aryl that is unsubstituted or substituted by one or more $C_1–C_6$alkyl groups or $C_1–C_6$alkoxy groups; or $C_7–C_{30}$aralkyl that is unsubstituted or substituted by one or more $C_1–C_6$alkyl groups or $C_1–C_6$alkoxy groups.

When any of the radicals $R_1$ to $R_{13}$ is/are $C_1–C_{18}$alkyl or $C_1–C_{18}$alkoxy, those radicals can be straight-chained or branched.

Examples of alkyl groups are methyl, ethyl, isopropyl, n-propyl, n-butyl, isobutyl, sec-butyl, tert-butyl and the various isomeric pentyl, hexyl, heptyl, octyl, nonyl, decyl, undecyl, dodecyl, tridecyl, tetradecyl, pentadecyl, hexadecyl, heptadecyl and octadecyl groups.

Suitable alkoxy groups are, for example, methoxy, ethoxy, isopropoxy, n-propoxy, n-butoxy, isobutoxy, sec-butoxy, tert-butoxy and the various isomeric pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy and octadecyloxy groups.

Examples of alkoxyalkyl groups are 2-methoxyethyl, 2-ethoxyethyl, 2-methoxypropyl, 3-methoxypropyl, 4-methoxybutyl and 4-ethoxybutyl.

Cycloalkyl is preferably $C_5–C_8$cycloalkyl, especially $C_5$- or $C_6$-cycloalkyl. Some examples thereof are cyclopentyl, methylcyclopentyl, cyclohexyl, cycloheptyl and cyclooctyl.

Aryl groups are, for example, phenyl, tolyl, mesityl, isityl, naphthyl and anthryl.

Aralkyl preferably contains from 7 to 12 carbon atoms and especially from 7 to 10 carbon atoms. It may be, for example, benzyl, phenethyl, 3-phenylpropyl, α-methylbenzyl, 4-phenylbutyl or α,α-dimethylbenzyl.

Preference is given to compounds of formula I or II wherein $R_1$ is $C_1–C_{12}$alkyl or $C_6–C_{10}$aryl, especially isopropyl, n-pentyl or phenyl.

Preference is also given to compounds of formula I wherein the radicals $R_2$ to $R_{13}$ are hydrogen.

A further preferred embodiment of the invention comprises compounds of formula I wherein at least two of the radicals $R_3$, $R_4$, $R_7$ and $R_8$ are alkoxy, —$NO_2$, dialkylamino, alkylthio, alkylsulfonyl or halogen.

Of those compounds, special preference is given to those wherein $R_3$ and $R_8$ are alkoxy or dialkylamino.

Special preference is given to halogen-free compounds of formula I, that is to say compounds of formula I wherein none of the radicals $R_2$ to $R_{13}$ is halogen.

The compounds of formula I can be prepared according to processes known per se. In the first reaction step, the iminomethylphenol of formula VII, wherein $R_1$, $R_{10}$, $R_{11}$, $R_{12}$ and $R_{13}$ are as defined above, is prepared from the known salicylaldehydes of formula V and the amines of formula VI.

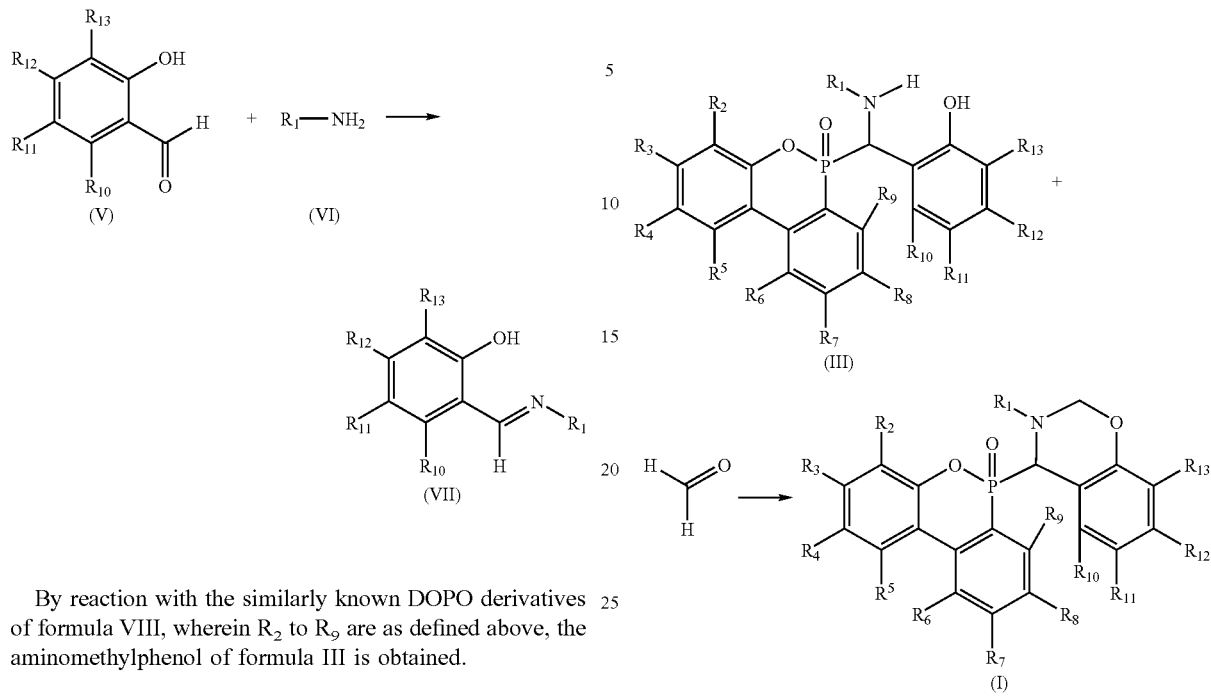

By reaction with the similarly known DOPO derivatives of formula VIII, wherein $R_2$ to $R_9$ are as defined above, the aminomethylphenol of formula III is obtained.

The reaction of III with formaldehyde finally yields the benzoxazines of formula I

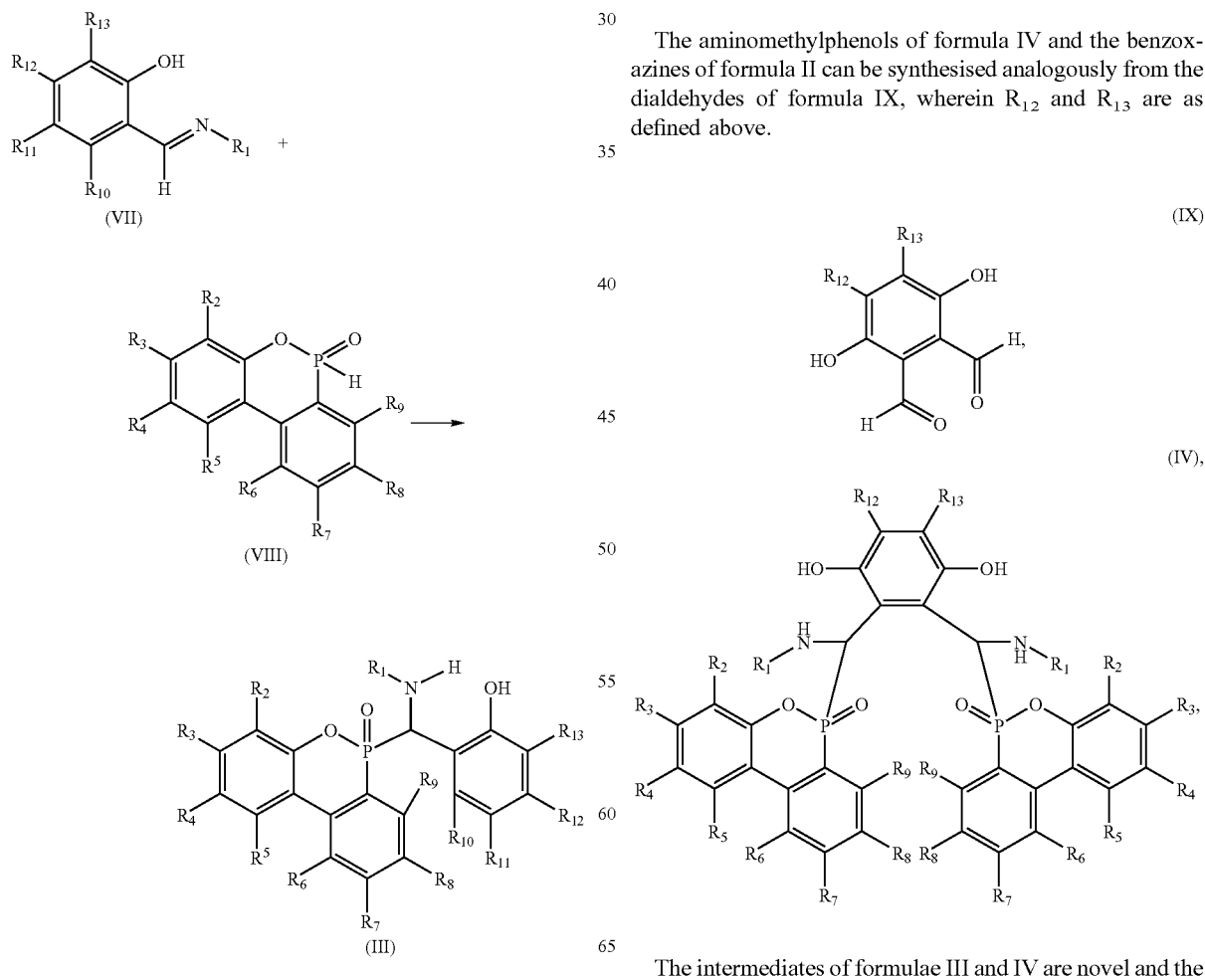

The aminomethylphenols of formula IV and the benzoxazines of formula II can be synthesised analogously from the dialdehydes of formula IX, wherein $R_{12}$ and $R_{13}$ are as defined above.

The intermediates of formulae III and IV are novel and the invention relates also thereto. The invention relates also to a process for the preparation of compounds of formula I or II, in which process a compound of formula III or IV is reacted with formaldehyde.

The reaction can be carried out in an organic solvent at elevated temperature, preferably from 40° C. to 160° C., especially from 60° C. to 100° C.

It is also possible, however, to react the compound of formula II with formaldehyde without solvent. In that process, it is advantageous to use solid paraformaldehyde, which is mixed with the compound of formula III or IV, also in solid form, to form a homogeneous powder. The mixture is then fused and maintained at the fusion temperature until the evolution of $CO_2$ has ceased.

The benzoxazines of formulae I and II and also the aminomethylphenols of formulae III and IV are distinguished by high inherent flame retardation. Mixing them into thermoplastic or thermosetting polymers yields matrix systems that have flame-retardant properties. Depending on the concentration of the benzoxazine or aminophenol in the resin blend, it is possible to obtain grades of from V0 to V1 according to the UL-94 standard.

The invention relates also to a composition comprising
(a) a thermoplastic or thermosetting resin and
(b) a compound of formula I, II, III or IV.

Component (b) in those compositions according to the invention is advantageously used in amounts of from 5 to 60% by weight, preferably from 10 to 50% by weight, especially from 15 to 40% by weight, based on the total amount of components (a)+(b).

As component (a), preference is given to the use of thermosetting resins, especially epoxy resins and oxazine resins.

Oxazine resins are described, for example, in GB-A 1 437 814.

The benzoxazines and aminophenols according to the invention are especially suitable as flame-proofing agents for epoxy resins.

The invention accordingly relates also to a composition comprising
(a) an epoxy resin,
(b) a compound of formula I or II or a compound of formula III or IV, and
(c) a hardener for the epoxy resin.

Component (b) in those compositions according to the invention is advantageously used in amounts of from 5 to 60% by weight, preferably from 10 to 50% by weight, especially from 15 to 40% by weight, based on the total amount of components (a)+(b)+(c).

In the compositions according to the invention, the benzoxazines of formula I or II or the aminomethylphenols of formula III or IV can be combined with other known flame-proofing agents, for example phosphate esters, phosphonate esters, phosphine oxides, aluminium trihydrate, calcined aluminium trihydrate, magnesium hydroxide, $Sb_2O_3$, complex compounds that split off water, and ammonium polyphosphate. The total amount of flame-proofing agent(s) is advantageously from 5 to 60% by weight, preferably from 10 to 50% by weight, especially from 15 to 40% by weight, based on the total amount (epoxy resin+flame-proofing agent(s)+hardener).

The epoxy resins customarily employed in epoxy resin technology are suitable as component A in the preparation of the compositions according to the invention. Examples of epoxy resins include:

I) polyglycidyl and poly(β-methylglycidyl) esters, obtainable by the reaction of a compound having at least two carboxyl groups in the molecule with epichlorohydrin or β-methylepichlorohydrin. The reaction is advantageously carried out in the presence of bases.

As a compound having at least two carboxyl groups in the molecule there can be used aliphatic polycarboxylic acids. Examples of such polycarboxylic acids are oxalic acid, succinic acid, glutaric acid, adipic acid, pimelic acid, suberic acid, azelaic acid and dimerised or trimerised linoleic acid.

It is also possible, however, to use cycloaliphatic polycarboxylic acids, for example tetrahydrophthalic acid, 4-methyltetrahydrophthalic acid, hexahydrophthalic acid or 4-methylhexahydrophthalic acid.

It is also possible to use aromatic polycarboxylic acids, for example phthalic acid, isophthalic acid or terephthalic acid.

II) polyglycidyl or poly(β-methylglycidyl) ethers, obtainable by the reaction of a compound having at least two free alcoholic hydroxy groups and/or phenolic hydroxy groups with epichlorohydrin or β-methylepichlorohydrin under alkaline conditions or in the presence of an acid catalyst with subsequent alkali treatment.

The glycidyl ethers of that type are derived, for example, from acyclic alcohols, e.g. from ethylene glycol, diethylene glycol or higher poly(oxyethylene) glycols, propane-1,2-diol or poly(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylolpropane, pentaerythritol, sorbitol, and from polyepichlorohydrins.

Further glycidyl ethers of that type are derived from cycloaliphatic alcohols, such as 1,4-cyclohexanedimethanol, bis(4-hydroxycyclohexyl)methane or 2,2-bis(4-hydroxycyclohexyl)-propane, or from alcohols that contain aromatic groups and/or further functional groups, such as N,N-bis(2-hydroxyethyl)aniline or p,p'-bis(2-hydroxyethylamino)diphenylmethane. The glycidyl ethers can be based also on mononuclear phenols, for example resorcinol or hydroquinone, or on polynuclear phenols, for example bis(4-hydroxyphenyl)methane, 4,4'-dihydroxybiphenyl, bis(4-hydroxyphenyl)sulfone, 1,1,2,2-tetrakis(4-hydroxyphenyl)ethane, 2,2-bis(4-hydroxyphenyl)propane or 2,2-bis(3,5-dibromo-4-hydroxyphenyl)propane.

Further suitable hydroxy compounds for the preparation of glycidyl ethers are novolaks, obtainable by the condensation of aldehydes, such as formaldehyde, acetaldehyde, chloral or furfuraldehyde, with phenols or bisphenols that are unsubstituted or substituted by chlorine atoms or by $C_1$–$C_9$alkyl groups, for example phenol, 4-chlorophenol, 2-methylphenol or 4-tert-butylphenol.

III) poly(N-glycidyl) compounds, obtainable by dehydrochlorination of the reaction products of epichlorohydrin and amines containing at least two amine hydrogen atoms. Those amines are, for example, aniline, n-butylamine, bis(4-aminophenyl)methane, m-xylylenediamine or bis(4-methylaminophenyl)methane.

The poly(N-glycidyl) compounds also include, however, triglycidyl isocyanurate, N,N'-diglycidyl derivatives of cycloalkylene ureas, such as ethylene urea or 1,3-propylene urea, and diglycidyl derivatives of hydantoins, such as of 5,5-dimethylhydantoin.

IV) poly(S-glycidyl) compounds, for example di-S-glycidyl derivatives that are derived from dithiols, for example ethane-1,2-dithiol or bis(4-mercaptomethylphenyl) ether.

V) cycloaliphatic epoxy resins, for example bis(2,3-epoxycyclopentyl) ether, 2,3-epoxycyclopentylglycidyl ether, 1,2-bis(2,3-epoxycyclopentyloxy)ethane or 3,4-epoxycyclohexylmethyl 3',4'-epoxycyclohexanecarboxylate.

It is also possible, however, to use epoxy resins in which the 1,2-epoxide groups are bonded to different hetero atoms or functional groups; such compounds include, for example, the N,N,O-triglycidyl derivative of 4-aminophenol, the glycidyl ether-glycidyl ester of salicylic acid, N-glycidyl-N'-(2-glycidyloxypropyl)-5,5-dimethylhydantoin and 2-glycidyloxy-1,3-bis(5,5-dimethyl-1-glycidylhydantoin-3-yl) propane.

For the preparation of the epoxy resin compositions according to the invention, preference is given to the use of a diglycidyl ether of a bisphenol, an epoxy novolak, a cycloaliphatic epoxy resin or a poly(N-glycidyl) compound.

Especially preferred epoxy resins are diglycidyl ether of bisphenol A, diglycidyl ether of bisphenol F, epoxyphenol novolaks, epoxycresol novolaks, 3,4-epoxycyclohexylmethyl 3',4'-epoxycyclohexanecarboxylate and N,N,N',N'-tetraglycidyldiaminodiphenylmethane.

As hardener (c), the epoxy resin compositions according to the invention can comprise the hardeners customarily employed in epoxy resin technology, for example polycarboxylic acids and anhydrides thereof, amines, polyamines, polyaminoamides, amino-group-containing adducts, guanidines, cyanoguanidines, aliphatic or aromatic polyols or catalytically active hardeners.

Suitable polycarboxylic acids that may be mentioned include, for example: aliphatic polycarboxylic acids, such as maleic acid, oxalic acid, succinic acid, nonyl- or dodecylsuccinic acid, glutaric acid, adipic acid, pimelic acid, suberic acid, azelaic acid and dimerised or trimerised linoleic acid; cycloaliphatic polycarboxylic acids, for example tetrahydrophthalic acid, methylendomethylenetetrahydrophthalic acid, hexachloroendomethylenetetrahydrophthalic acid, 4-methyltetrahydrophthalic acid, hexahydrophthalic acid and 4-methylhexahydrophthalic acid, and aromatic polycarboxylic acids, for example phthalic acid, isophthalic acid, terephthalic acid, trimellitic acid, pyromellitic acid and benzophenone-3,3',4,4'-tetracarboxylic acid, and the anhydrides of the mentioned polycarboxylic acids.

As polyamines for curing, there can be used aliphatic, cycloaliphatic, aromatic or heterocyclic amines, for example ethylenedlamine, propane-1,2-diamine, propane-1,3-diamine, N,N-diethylethylenediamine, hexamethylenediamine, diethylenetriamine, triethylenetetramine, tetraethylenepentamine, N-(2-hydroxyethyl)-, N-(2-hydroxypropyl)- and N-(2-cyanoethyl)-diethyltriamine, 2,2,4-trimethylhexane-1,6-diamine, 2,3,3-trimethylhexane-1,6-diamine, N,N-dimethyl- and N,N-diethyl-propane-1,3-diamine, ethanolamine, m- and p-phenylenediamine, bis(4-aminophenyl) methane, aniline-formaldehyde resin, bis(4-aminophenyl) sulfone, m-xylylenediamine, bis(4-aminocyclohexyl) methane, 2,2-bis(4-aminocyclohexyl)propane, 2,2-bis (4-amino-3-methylcyclohexyl)propane, 3-aminomethyl-3,5, 5-trimethylcyclohexylamine (isophoronediamine) and N-(2-aminoethyl)piperazine, and as polyaminoamides, for example, those from aliphatic polyamines and dimerised or trimerised fatty acids.

Suitable as polyaminoamides are, for example, the reaction products obtained by the reaction of polycarboxylic acids, preferably of dimerised fatty acids, with polyamines in a molar excess, as described, for example, in the Handbook of Epoxy Resins, 1967, pages 10-2 to 10-10, by H. Lee and K. Neville.

Amino-group-containing adducts of an amine and a polyepoxy compound used as hardeners for epoxy resins are also known and can be used to cure the epoxy resin compositions according to the invention and are obtained, for example, by the reaction of epoxy resins with polyamines in an equivalent excess. Such amino-group-containing adducts are described in greater detail, for example, in U.S. Pat. Nos. 3,538,184; 4,330,659; 4,500,582 and 4,540,750.

Further suitable amine hardeners are dicyandiamide, guanidines, for example 1-o-tolylbiguamide, cyanoguanidines, such as, for example, the compounds described in U.S. Pat. No. 4,859,761 or EP-A 306,451, or modified polyamines, such as Ancamine 2014 S (Anchor Chemical UK Limited, Manchester).

Also suitable are N-acylimidazoles, such as 1-(2',4',6'-trimethylbenzoyl)-2-phenylimidazole and 1-benzoyl-2-isopropylimidazole. Such compounds are described, for example, in U.S. Pat. Nos. 4,436,892 and 4,587,311.

Suitable aliphatic polyols for curing the epoxy resin compositions according to the invention are, for example, ethylene glycol, diethylene glycol and higher poly(oxyethylene) glycols, propane-1,2-diol and poly(oxypropylene) glycols, propane-1,3-diol, butane-1,4-diol, poly-(oxytetramethylene) glycols, pentane-1,5-diol, hexane-1,6-diol, hexane-2,4,6-triol, glycerol, 1,1,1-trimethylolpropane, pentaerythritol, sorbitol, N,N-bis(2-hydroxyethyl)aniline and p,p'-bis(2-hydroxyethylamino)diphenylmethane.

As aromatic polyols for curing, there can be used, for example, mononuclear phenols, such as resorcinol, hydroquinone, or polynuclear phenols, such as bis(4-hydroxyphenyl)methane, 4,4'-dihydroxyblphenyl, bis(4-hydroxyphenyl) sulfone, 1,1,2,2-tetrakis(4-hydroxyphenyl)-ethane, 2,2-bis (4-hydroxyphenyl)propane, 2,2-bis(3,5-dibromo-4-hydroxyphenyl)propane, and novolaks, obtainable by condensation of aldehydes, such as formaldehyde, acetaldehyde, chloral or furfuraldehyde, with phenols, such as phenol, or with phenols that are substituted in the nucleus by chlorine atoms or by $C_1$–$C_9$alkyl groups, for example 4-chlorophenol, 2-methylphenol, or 4-tert-butylphenol, or by condensation with bisphenols of the type mentioned above.

It is also possible to use catalytically active hardeners for curing the epoxy resin compositions according to the invention, such as tertiary amines, for example 2,4,6-tris-(dimethylaminomethyl)phenol and other Mannich bases, N-benzyldimethylamine and triethanolamine; alkali metal alkanolates of alcohols, for example sodium alcoholate of 2,4-dihydroxy-3-hydroxymethylpentane; tin salts of alkanoic acids, for example tin octanoate; Friedel-Crafts catalysts, for example boron trifluoride and its complexes, for example boron trifluoride-amine complexes, and chelates that are obtained by reacting boron trifluoride with, for example, 1,3-diketones, sulfonium salts, as disclosed, for example, in EP Patent 0 379 464 or U.S. Pat. No. 5,013,814, in EP Patent 0 580 552 or U.S. Pat. No. 5,374,697, or heterocylic ammonium salts, for example quinolinium salts mixed with benzopinacol, as mentioned, for example, in EP-A-0 066 543.

Preference is given to the use of an anhydride or dicyandiamide as hardener (c).

Special preference Is given to tetrahydrophthalic anhydride, methyltetrahydrophthalic anhydride, hexahydrophthalic anhydride, methylhexahydrophthalic anhydride, dicyandiamide and novolaks.

The amount of hardener used will depend upon the chemical nature of the hardener and upon the desired properties of the curable mixture and of the cured product. The maximum amount can be determined readily by a person skilled in the art. When the hardener is an amine, generally from 0.75 to 1.25 equivalents of amine hydrogen per epoxy equivalent are used, When polycarboxylic acids or anhydrides thereof are used, usually from 0.4 to 1.1 equivalents of carboxyl group or anhydride group per epoxy equivalent are used. When polyphenols are used as hardeners, from 0.75 to 1.25 phenolic hydroxyl groups per 1 epoxy equivalent are used. Catalytically active hardeners are generally used in amounts of from 0.1 to 40 parts by weight per 100 parts by weight of epoxy resin.

Where appropriate, the substance mixtures according to the invention can also comprise accelerators (d) for the crosslinking reaction with the latent hardener. Suitable accelerators (d) are, for example, urea derivatives, such as N,N-dimethyl-N'-(3-chloro-4-methylphenyl)urea (chlorotoluron), N,N-dimethyl-N'-(4-chlorophenyl)urea (monuron) or N,N-dimethyl-N'-(3,4-dichlorophenyl)urea (diuron), 2,4-bis (N',N'-dimethylureido)toluene or 1,4-bis(N',N'-dimethylureido)benzene. The use of such compounds is described, for example, in the above-mentioned U.S. Pat. No. 4,283,520. Suitable accelerators are, for example, the urea derivatives described in GB-A 1 192 790.

Suitable accelerators are also imidazoles, such as imidazole, 2-ethylimidazole, 2-phenylimidazole, 2-methylimidazole, 1-methylimidazole, 1-cyanoethyl-2-ethyl-4-methylimidazole or 2-ethyl-4-methylimidazole.

Further suitable accelerators are also tertiary amines, and salts or quaternary ammonium compounds thereof, such as benzyldimethylamine, 2,4,6-tris(dimethylaminomethyl)phenol, 4-aminopyridine, tripentylammonium phenolate, tetramethylammonium chloride or benzyltributylammonium bromide or chloride; or alkali metal alcoholates, such as sodium alcoholates of 2,4-dihydroxy-3-hydroxymethylpentane.

The epoxy resin compositions according to the invention can also comprise the inorganic and organic fillers and reinforcing materials that are customarily employed in epoxy resin technology. As fillers there come into consideration, for example, the following: mineral and fibrous fillers, such as quartz powder, fused silica, aluminium oxide, glass powder, mica, kaolin, dolomite, graphite, carbon black, and carbon fibres and textile fibres. Preferred fillers are quartz powder, fused silica, aluminium oxide or dolomite. Suitable reinforcing materials are, for example, glass fibres, carbon fibres, Kevlar fibres and hybrids thereof.

The epoxy resin compositions according to the invention are prepared according to methods known per se, such as using known mixing equipment, for example stirrers, kneaders, rollers or, in the case of solid substances, dry mixers.

The epoxy resin compositions according to the invention are cured to form mouldings, coatings or the like in a manner customary in epoxy resin technology, as described, for example, in "Handbook of Epoxy Resins", 1967, by H. Lee and K. Neville.

The invention relates also to the resulting cured products.

The use of benzoxazines of formula I or II or of aminomethylphenols of formula III or IV as flame-proofing agents enables the preparation of resins having a high degree of flame-retardation, a high glass transition temperature and very good heat resistance. This is surprising because generally the flame-proofing effect produced by the addition of additives is obtained at the cost of a deterioration in the mechanical properties and especially a decrease in the glass transition temperature.

The compounds of formulae III and IV and those compounds of formulae I and II having at least two active hydrogen atoms can also act as hardeners for epoxy resins.

The invention accordingly relates also to the use of a compound of formula III or IV as a hardener for epoxy resins.

The compositions according to the invention are suitable especially for the manufacture of prepregs, laminates and RTM (resin transfer moulding) systems.

EXAMPLES

In the Examples that follow, the following substances are used:
Epoxy resin 1: liquid diglycidyl ether of bisphenol A (epoxy content: 5.5 eq./kg)
Epoxy resin 2: liquid diglycidyl ether of bisphenol A (epoxy content: 5.2–5.4 eq./kg)
Epoxy resin 3: tetraglycidyldiaminodiphenylmethane (epoxy content: 7.5–8.5 eq./kg)
Epoxy resin 4: (3,4-epoxycyclohexyl)methyl 3,4-epoxycyclohexanecarboxylate (epoxy content 7.0–7.6 eq./kg)

Preparation Examples

I.1. Compound of Formula IIIa

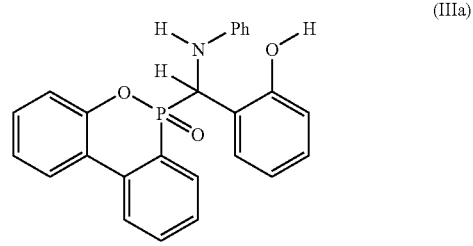

(Ph = phenyl)

600 ml of tetrahydrofuran are placed in a 1.5 liter sulfonating flask having a reflux condenser, an internal thermometer, a dropping funnel and a KPG stirrer. 110.25 g (0.51 mol) of Struktol PD 3710 are added with stirring. On heating the white suspension at 60–65° C., a slightly cloudy colourless solution is obtained at an internal temperature of about 40° C. At an internal temperature of about 60° C., 102.65 g (0.51 mol) of 2-(phenylimino)methylphenol dissolved in 350 ml of tetrahydrofuran are then added dropwise over a period of 30 minutes. Progress of the reaction is monitored hourly by means of thin-layer chromatography (silica gel, THF/dichloromethane=8:2). In the course of boiling for seven hours with gentle reflux, pronounced precipitation of a white solid is observed. After that time, thin-layer chromatography shows that there is no remaining starting material. The white solid is filtered off over a frit, and the mother liquor is concentrated using a rotary evaporator. The product that precipitates therefrom and the previously isolated solid are dried in vacuo at from 40° C. to 50° C. and at 0.15 mbar for about 10 hours. Yield: 229 g (<95% of theory)

DSC Analysis (Rate of Heating 10 K/min, Temperature Range −50° C. to 300° C.):
Endotherms from 75° C. to 140° C., ΔH=−90 J/g and from 160° C. to 210° C., ΔH=−109 J/g IR (KBr Dellet):
3428.6 cm$^{-1}$, 3267.4 cm$^{-1}$, 3061.13 cm$^{-1}$, 2960.48 cm$^{-1}$, 2872.21 cm$^{-1}$, 2735.07 cm$^{-1}$, 2599.83 cm$^{-1}$, 1945.96 cm$^{-1}$, 1915.66 cm$^{-1}$, 1604.26 cm$^{-1}$, 1562.21 cm$^{-1}$, 1525.24 cm$^{-1}$, 1499.71 cm$^{-1}$, 1476.76 cm$^{-1}$, 1456.7 cm$^{-1}$, 1431.74 cm$^{-1}$, 1376.5 cm$^{-1}$, 1369.8 cm$^{-1}$, 1313.11 cm$^{-1}$, 1271 cm$^{-1}$, 1224.16 cm$^{-1}$, 1206.76 cm$^{-1}$, 1146.37 cm$^{-1}$, 1117.95 cm$^{-1}$, 1083.39 cm$^{-1}$, 1047.44 cm$^{-1}$, 994.36 cm$^{-1}$, 925.02 cm$^{-1}$, 889.51 cm$^{-1}$, 850.23 cm$^{-1}$, 827.54 cm$^{-1}$, 788.96 cm$^{-1}$, 755.12 cm$^{-1}$, 715.31 cm$^{-1}$, 691.38 cm$^{-1}$, 633.07 cm$^{-1}$, 618.01 cm$^{-1}$, 602.96 cm$^{-1}$, 570.11 cm$^{-1}$, 558.45 cm$^{-1}$.

| | $^1$H—NMR, $^{13}$C—NMR, $^{31}$P—NMR: | | | | | |
|---|---|---|---|---|---|---|
| Position | $^1$H/ppm | M | J | H | $^{13}$C/ppm | $^{31}$P/ppm |
| Isomer 1: | | | | | | |
| 1 | 9.56 | s | | 1H | 155.3 | |
| 2 | 6.76 | t | 8.3 Hz | 1H | 114.4 | |
| 3 | 7.05 | t | 7.75 Hz | 1H | 128.5 | |
| 4 | 6.74 | t | 7.5 Hz | 1H | 118.8 | |
| 5 | 7.50 | d | 7.5 Hz | 1H | 129.3 | |
| 6 | 5.25 | dd | 10 Hz, 15 Hz | 1H | 49.0 | |
| 7 | | | | | 121.0 | |
| 8 | | | | | 123.7 | 31.271 |
| 9 | 8.01 | dd | 7.5 Hz, 0.5 Hz | 1H | 131.81 | |
| 10 | 7.55 | dt | 7.5 Hz, 2.5 Hz | 1H | 128.2 | |
| 11 | 7.74 | t | 7.7 Hz | 1H | 133.9 | |
| 12 | 8.18 | dd | 10 Hz, 5 Hz | 1H | 123.3 | |
| 13 | | | | | 135.1 | |
| 14 | | | | | 121.1 | |
| 15 | 8.13 | d | | | 125.3 | |
| 16 | 7.28 | dd | | | 124.9 | |
| 17 | 7.40 | t | 7.5 Hz | 1H | 130.4 | |
| 18 | 6.99 | d | 7.5 Hz | 1H | 120.2 | |
| 19 | | | | | 149.3 | |
| 20 | N—H | | | | | |
| 21 | | | | | 146.9 | |
| 22 | 6.91 | t | 7.5 Hz | 1H | 113.1 | |
| 23 | 6.59 | t | 7.5 Hz | 1H | 128.6 | |
| 24 | 6.48 | t | | | 117.0 | |
| 25 | 6.59 | t | 7.5 Hz | 1H | 128.6 | |
| 26 | 6.91 | t | 7.5 Hz | 1H | 113.1 | |
| Isomer 2: | | | | | | |
| 1 | 9.43 | s | | 1H | 155.1 | |
| 2 | 6.53 | t | 7.5 Hz | 1H | 114.4 | |
| 3 | 6.97 | t | 7.5 Hz | 1H | 128.6 | |
| 4 | 6.74 | t | 7.5 Hz | 1H | 118.5 | |
| 5 | 7.47 | d | 7.5 Hz | 1H | 128.7 | |
| 6 | 5.42 | dd | 10 Hz, 15 Hz | 1H | 42.4 | |
| 7 | | | | | 121.2 | |
| 8 | | | | | 123.1 | 27.986 |
| 9 | 7.30 | dd | 7.5 Hz, 1.0 Hz | 1H | 130.5 | |
| 10 | 7.34 | dt | 7.5 Hz, 2.5 Hz | 1H | 127.9 | |
| 11 | 7.7 | t | 7.5 Hz | 1H | 133.4 | |
| 12 | 8.13 | dd | 7.5 Hz, 1 Hz | 1H | 123.3 | |
| 13 | | | | | 135.9 | |
| 14 | | | | | 122.2 | |
| 15 | 8.12 | d | | | 125.3 | |
| 16 | 7.31 | dd | | | 124.7 | |
| 17 | 7.40 | t | 7.5 Hz | 1H | 130.4 | |
| 18 | 7.17 | d | 7.5 Hz | 1H | 119.9 | |
| 19 | | | | | 148.8 | |
| 20 | N—H | | | | | |
| 21 | | | | | 147.0 | |
| 22 | 6.59 | d | | | 113.1 | |
| 23 | 6.95 | d | | | 128.6 | |
| 24 | 6.48 | d | | | 117.0 | |
| 25 | 6.95 | d | | | 128.6 | |
| 26 | 6.59 | d | | | 113.1 | |

The product is a mixture of the diastereoisomers IIIa1 and IIIa2

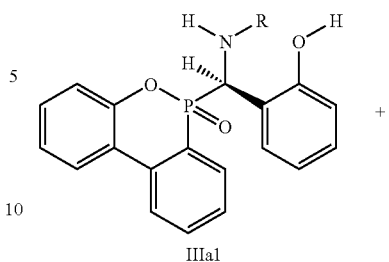

IIIa1

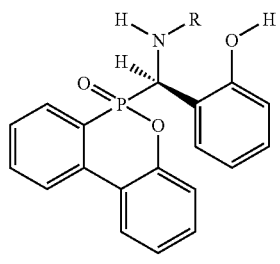

IIIa2

I.2. Compound of Formula Ia

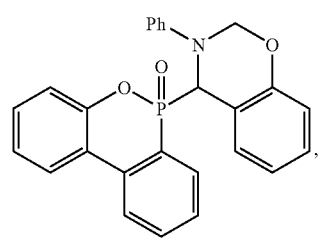

(Ia)

(Ph = phenyl)

Variant 1:

2.0 g (4.8 mmol) of the compound of formula IIIa prepared in Example I.1 in 50 ml chloroform are placed in a 100 ml sulfonating flask having a reflux condenser, KPG stirrer and internal thermometer and boiled at reflux, yielding a slightly cloudy colourless solution. After the addition of 5–6 grains of a UOP molecular sieve, Type 4A, 2.2–4.9 mm, 0.15 g (4.8 mmol) of paraformaldehyde is added with stirring. The solution is boiled at gentle reflux, and after one hour the thin-layer chromatogram shows that the reaction conversion is complete. The batch is filtered while hot, and the resulting clear colourless solution is concentrated using a rotary evaporator. The crude product consists of 2.0 g of colourless crystals, which are dried in an oil pump vacuum (50° C./0.5 mbar /2 hours).

Yield: 1.8 g of white crystals (88%).

Variant 2:

50 g (0.121 mol) of the compound of formula IIIa prepared in Example I.1 are pulversed in a mortar, and 7.6 g (0.242 mol) of paraformaldehyde are added thereto.

Both components are triturated to form a homogeneous powder. The powder is distributed into 12 small aluminium crucibles, which are then placed on a gelling time plate at a temperature of 200° C.

After about 10 minutes' stirring, a clear yellowish solution Is obtained. After cooling, 42.51 g (82%) of a whiteish-yellow powder are obtained.

DSC (Rate of Heating −50° C. to 400° C. 10 K/min):
$T_g$=60° C., pre-crystallisation about ΔH=15 J/g, melting range ΔH=18 J/g, reaction ΔH=196 J/g IR (KBr pellet): 3437.08 cm$^{-1}$, 3060.31 cm$^{-1}$, 2904.92 cm$^{-1}$, 1604.9 cm$^{-1}$, 1594.3 cm$^{-1}$, 1581.01 cm$^{-1}$, 1558.1 cm$^{-1}$, 1489.78 cm$^{-1}$, 1471.86 cm$^{-1}$, 1447.05 cm$^{-1}$, 1428.4 cm$^{-1}$, 1364.92 cm$^{-1}$, 1313.02 cm$^{-1}$, 1268.4 cm$^{-1}$, 1256.68 cm$^{-1}$, 1225.86 cm$^{-1}$, 1211.06 cm$^{-1}$, 1202.06 cm$^{-1}$, 1186.64 cm$^{-1}$, 1147.61 cm$^{-1}$, 1116.19 cm$^{-1}$, 1081.49 cm$^{-1}$, 1041.29 cm$^{-1}$, 1029.37 cm$^{-1}$, 999.42 cm$^{-1}$, 976.64 cm$^{-1}$, 955.96 cm$^{-1}$, 909.71 cm$^{-1}$, 876.99 cm$^{-1}$, 807.49 cm$^{-1}$, 781.05 cm$^{-1}$, 774.10 cm$^{-1}$, 761.64 cm$^{-1}$, 753.45 cm$^{-1}$, 716.86 cm$^{-1}$, 709.37 cm$^{-1}$, 695.75 cm$^{-1}$, 686.85 cm$^{-1}$, 637.21 cm$^{-1}$, 612.93 cm$^{-1}$, 592.25 cm$^{-1}$, 565.20 cm$^{-1}$, 552.46 cm$^{-1}$, 532.80 cm$^{-1}$, 515.19 cm$^{-1}$, 496.76 cm$^{-1}$, 465.78 cm$^{-1}$, 439.31 cm$^{-1}$.

$^1$H-NMR (DMSO): 5.21 ppm (d, 1H, $J_{H-P}$=15 Hz); 5.44 ppm (dd,1H, J=12.5 Hz, J=2.5 Hz; 5.54 ppm (d, 1H, J=12.5 Hz); 6.75 ppm (d, 2H, J=7.5 Hz); 6.84 ppm (q, 1H, J=5 Hz); 6.86 ppm (t,1H, J=2.5 Hz); 7.01 ppm (t, 1H, J=7.5 Hz); 7.09 ppm (t, 2H, J=7.5 Hz); 7.22 ppm (t, 1H, J=7.5 Hz); 7.3 ppm (d, 1H, J=7.5 Hz); 7.35 ppm (t, 1H, J=7.5 Hz); 7.38 ppm (d, 1H, J=7.5 Hz); 7.51 ppm (t, 1H, J=7.5 Hz); 7.55 ppm (dt,1H, J=2.5 Hz, J=7.5 Hz); 7.83 ppm (t, 1H, J=7.5 Hz); 7.88 ppm (dd, 1H, J=7.5 Hz, J=7.5 Hz); 8.27 ppm (d, 1H, J=1.2 Hz); 8.32 ppm (dd, 1H, J=5 Hz, J=5 Hz)

$^{31}$P-NMR (DMSO): 25.70 ppm (s); 25.80 ppm (I); 29.109 ppm (s); 29.201 ppm; 32.584 ppm (s)

II. Application Examples

Test specimens (4 mm plates) are prepared from tetraglycidyidiaminodiphenylmethane (TGDADPM, epoxy content: 7.5–8.5 eq./kg), the benzoxazine Ia prepared in Example I.2, dicyandiamide and 2-methylimidazole; the amounts used, the curing conditions and the gelling times are given in Table 1.

After removal from the moulds, the test specimens are tested for their combustibility according to UL 94 standard. The glass transition temperature $T_g$ is determined by means of differential scanning calorimetry (DSC); some of the test specimens are subjected to the pressure cooker test.

The results measured are compiled in Table 1.

Pressure Cooker Test:

The test specimens are placed in a rack in an autoclave; A sufficient amount of distilled water is then introduced, and the apparatus is sealed and heated. By using a thermometer having a thermostat and contact-maker, the heating output is so controlled that the temperature is 121° C. The pressure is set at about from 2.4 to 2.6 atm. The test plates are treated for 1 hour in the autoclave. After cooling, the water-uptake of the samples is measured.

TABLE 1

| Example | II.1 | II.2 | II.3 | II.4 | II.5 | II.6 | II.7 | II.8 |
|---|---|---|---|---|---|---|---|---|
| TGDADPM [g] | 80 | 80 | 85 | 85 | 80 | 80 | 80 | 50 |
| Benzoxazine Ia [g] | 20 | 20 | 15 | 15 | 20 | 20 | 20 | 50 |
| Dicyandiamide [g] | 3.5 | 3.5 | 3.5 | 3.5 | 3.5 | 3.5 | 2.0 | 2.0 |
| 2-Methylimidazole [g] | 0.5 | 0.5 | 0.5 | 0.5 | 0.5 | 0.25 | — | — |
| Gelling time (171° C.) | 450 s (171° C.) | 420 s (171° C.) | 400 s (171° C.) | 130 s (171° C.) | 330 s (171° C.) | 340 s (171° C.) | 360 s (190° C.) | 245 s (180° C.) |
| Curing cycle | 1 h/170° C. 1 h/200° C. | 1 h/170° C. 1 h/200° C. | 1 h/170° C. 1 h/200° C. | 1 h/170° C. 1 h/200° C. | 1 h/170° C. 1 h/200° C. | 1 h/170° C. 1 h/200° C. | 1 h/190° C. 1 h/200° C. | 1 h/190° C. 1 h/200° C. |
| $T_g$ [° C.] | 200 | 197 | 199 | 193 | 195 | 173 | 178 | |
| Water uptake | 0.48% | 0.60% | 0.58% | 0.30% | | | | |
| UL 94 | V1 | V1 | V1 | V1 | V1 | V1 | V1 | V0 |
| Total duration of combustion | 109 s | 106 s | 109 s | 104 s | 117 s | 101 s | 129 s | 13 s |

What is claimed is:

1. A compound of formula I or II

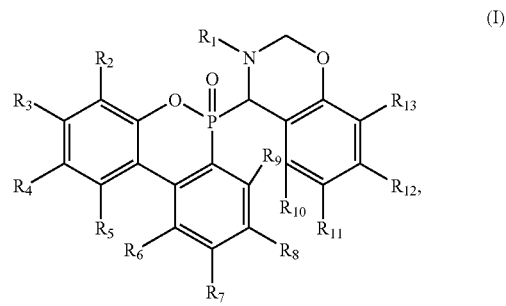

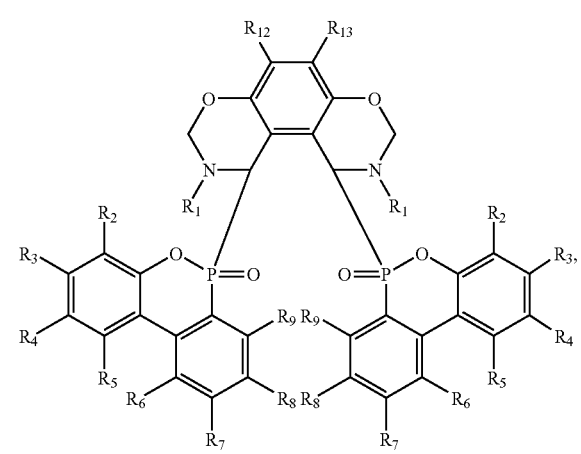

wherein $R_1$ is $C_1$–$C_{18}$ alkyl; $C_5$–$C_{12}$ cycloalkyl that is unsubstituted or substituted by one or more $C_1$–$C_6$ alkyl groups or $C_1$–$C_6$ alkoxy groups; $C_5$–$C_{22}$ aryl that is unsubstituted or substituted by one or more $C_1$–$C_6$ alkyl groups or $C_1$–$C_6$ alkoxy groups; or $C_7$–$C_{30}$ aralkyl that is unsubstituted or substituted by one or more $C_1$–$C_6$ alkyl groups or $C_1$–$C_6$ alkoxy groups and the radicals $R_2$ to $R_{13}$ are each independently of the other hydrogen; —$NO_2$; dialkylamino; alkylthio; alkylsulfonyl; halogen; $C_1$–$C_{18}$ alkyl; $C_1$–$C_{18}$ alkoxy; $C_1$–$C_{18}$ alkoxyalkyl; $C_5$–$C_{12}$ cycloalkyl that is unsubstituted or substituted by one or more $C_1$–$C_6$ alkyl groups or $C_1$–$C_6$ alkoxy groups; $C_5$–$C_{22}$ aryl that is unsubstituted or substituted by one or more $C_1$–$C_6$ alkyl groups or $C_1$–$C_6$ alkoxy groups; or $C_7$–$C_{30}$ aralkyl that is unsubstituted or substituted by one or more $C_1$–$C_6$ alky groups or $C_1$–$C_6$ alkoxy groups.

2. A compound of formula I or II according to claim 1, wherein $R_1$ is $C_1$–$C_{12}$ alkyl or $C_6$–$C_{10}$ aryl.

3. A compound of formula I or II according to claim 1, wherein $R_1$ is isopropyl, n-pentyl or phenyl.

4. A compound of formula I or II according to claim 1, wherein the radicals $R_2$ to $R_{13}$ are hydrogen.

5. A compound of formula I or II according to claim 1, wherein at least two of the radicals $R_3$, $R_4$, $R_7$ and $R_8$ are alkoxy, —$NO_2$, dialkylamino, alkylthio, alkylsulfonyl or halogen.

6. A compound of formula I or II according to claim 1, wherein $R_3$ and $R_8$ are alkoxy or dialkylamino.

7. A compound of formula I or II according to claim 1, wherein none of the radicals $R_2$ to $R_{13}$ is a halogen.

8. A process for the preparation of a compound of formula I or II according to claim 1, wherein a compound of formula III or IV

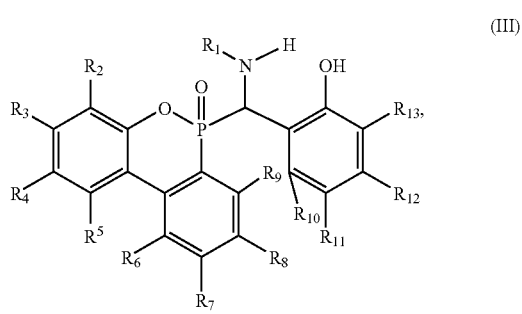

(III)

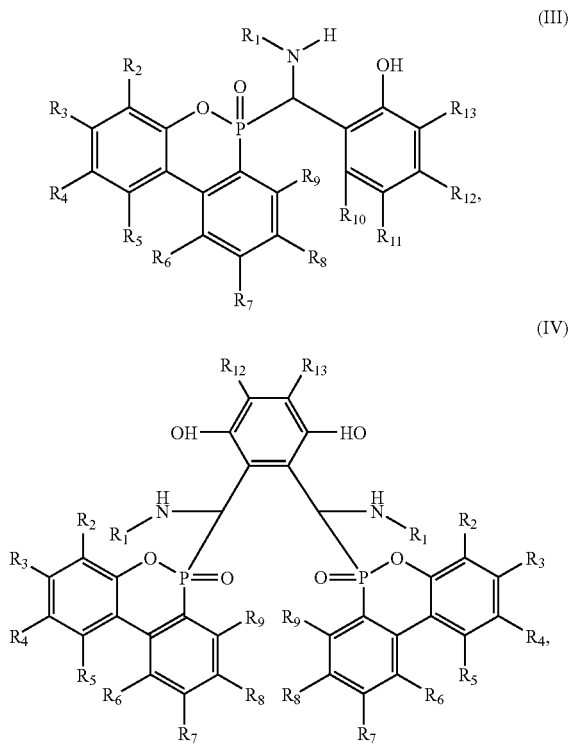

(IV)

wherein $R_1$ is $C_1$–$C_{18}$ alkyl; $C_5$–$C_{12}$ cycloalkyl that is unsubstituted or substituted by one or more $C_1$–$C_6$ alkyl groups or $C_1$–$C_6$ alkoxy groups; $C_5$–$C_{22}$ aryl that is unsubstituted or substituted by one or more $C_1$–$C_6$ alkyl groups or $C_1$–$C_6$ alkoxy groups; or $C_7$–$C_{30}$ aralkyl that is unsubstituted or substituted by one or more $C_1$–$C_6$ alkyl groups or $C_1$–$C_6$ alkoxy groups and the radicals $R_2$ to $R_{13}$ are each independently of the other hydrogen; —$NO_2$; dialkylamino; alkylthio; alkylsulfonyl; halogen; $C_1$–$C_{18}$ alkyk; $C_1$–$C_{18}$ alkoxy; $C_1$–$C_{18}$ alkoxyalkyl; $C_5$–$C_{12}$ cycloalkyl that is unsubstituted or substituted by one or more $C_1$–$C_6$ alkyl groups or $C_1$–$C_6$ alkoxy groups; $C_5$–$C_{22}$ aryl that is unsubstituted or substituted by one or more $C_1$–$C_6$ alkyl groups or $C_1$–$C_6$ alkoxy groups; or $C_7$–$C_{30}$ aralkyl that is unsubstituted or substituted by one or more $C_1$–$C_6$ alkyl groups or $C_1$–$C_6$ alkoxy groups is reacted with formaldehyde.

9. A process according to claim 8 wherein the reaction is carried out in an organic solvent at a temperature of from 40° C. to 160° C.

10. A process according to claim 8 wherein the reaction is carried out in an organic solvent at a temperature of from 60° C. to 100° C.

11. A compound of formula III or IV

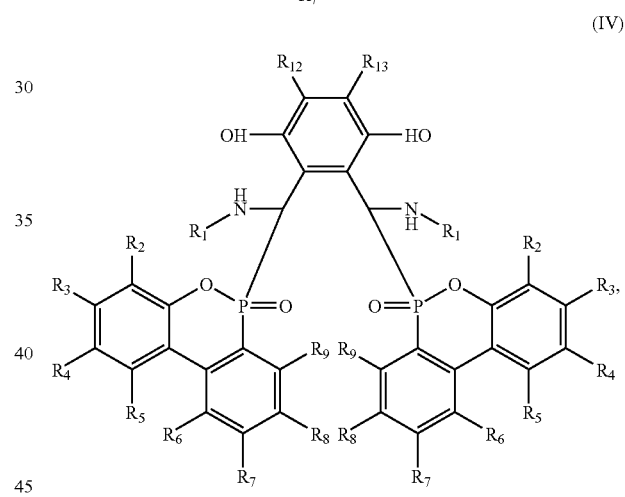

wherein $R_1$ is $C_1$–$C_{18}$ alkyl; $C_5$–$C_{12}$ cycloalkyl that is unsubstituted or substituted by one or more $C_1$–$C_6$ alkyl groups or $C_1$–$C_6$ alkoxy groups; $C_5$–$C_{22}$ aryl that is unsubstituted or substituted by one or more $C_1$–$C_6$ alkyl groups or $C_1$–$C_6$ alkoxy groups; or $C_7$–$C_{30}$ aralkyl that is unsubstituted or substituted by one or more $C_1$–$C_6$ alkyl groups or $C_1$–$C_6$ alkoxy groups and the radicals $R_2$ to $R_{13}$ are each independently of the other hydrogen; —$NO_2$; dialkylamino; alkylthio; alkylsulfonyl; halogen; $C_1$–$C_{18}$ alkyl; $C_1$–$C_{18}$ alkoxy; $C_1$–$C_{18}$ alkoxyalkyl; $C_5$–$C_{12}$ cycloalkyl that is unsubstituted or substituted by one or more $C_1$–$C_6$ alkyl groups or $C_1$–$C_6$ alkoxy groups; $C_5$–$C_{22}$ aryl that is unsubstituted or substituted by one or more $C_1$–$C_6$ alkyl groups or $C_1$–$C_6$ alkoxy groups; or $C_7$–$C_{30}$ aralkyl that is unsubstituted or substituted by one or more $C_1$–$C_6$ alkyl groups or $C_1$–$C_6$ alkoxy groups.

12. A composition comprising
(a) an epoxy resin; and
(b) a hardener comprising a compound of formula I, II, III or IV

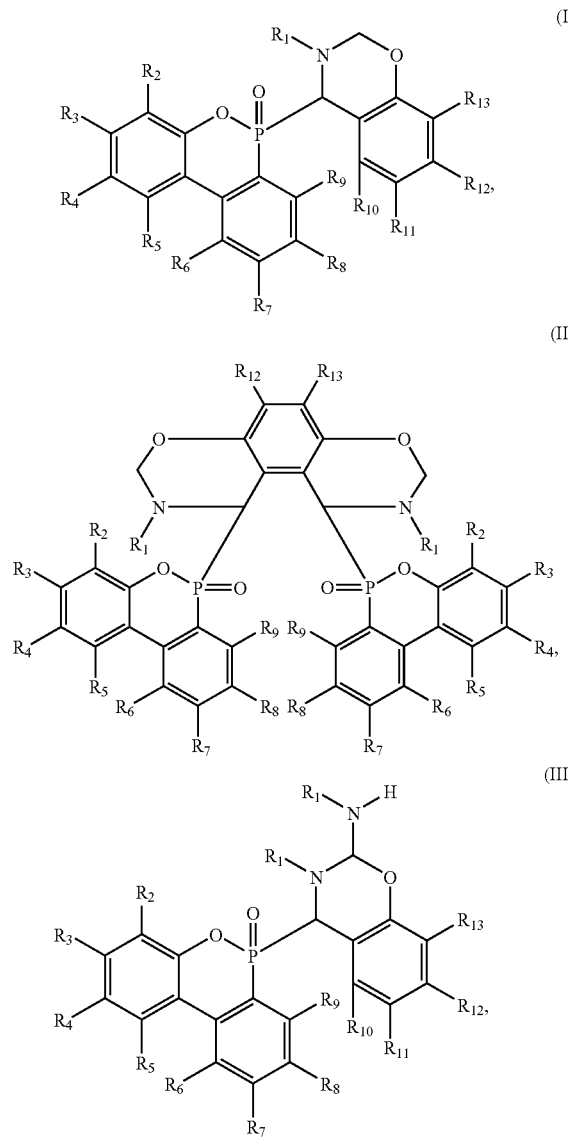
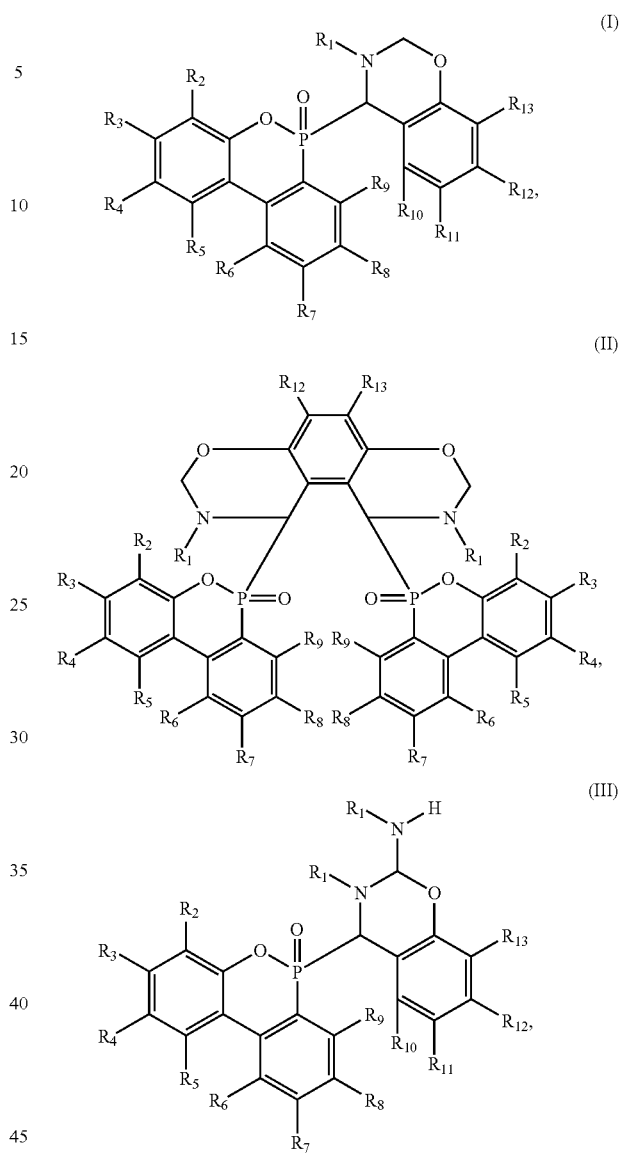

wherein the compound of formula I or II has at least two active hydrogen atoms and wherein $R_1$ is $C_1$–$C_{18}$ alkyl; $C_5$–$C_{12}$ cycloalkyl that is unsubstituted or substituted by one or more $C_1$–$C_6$ alkyl groups or $C_1$–$C_6$ alkoxy groups; $C_5$–$C_{22}$ that is unsubstituted or substituted by one or more $C_1$–$C_6$ alkyl groups or $C_1$–$C_6$ alkoxy groups; or $C_7$–$C_{30}$ aralkyl that is unsubstituted or substituted by one or more $C_1$–$C_6$ alkyl groups or $C_1$–$C_6$ alkoxy groups and the radicals $R_2$ to $R_{13}$ are each independently of the other hydrogen; —$NO_2$; dialkylamino; alkylthio; alkylsulfonyl; halogen; $C_1$–$C_{18}$ alkyl; $C_1$–$C_{18}$ alkoxy; $C_1$–$C_{18}$ alkoxyalkyl; $C_5$–$C_{12}$ cycloalkyl that is unsubstituted or substituted by one or more $C_1$–$C_6$ alkyl groups or $C_1$–$C_6$ alkoxy groups; $C_5$–$C_{22}$ aryl that is unsubstituted or substituted by one or more $C_1$–$C_6$ alkyl groups or $C_1$–$C_6$ alkoxy groups; or $C_7$–$C_{30}$ aralkyl that is unsubstituted or substituted by one or more $C_1$–$C_6$ alkyl groups or $C_1$–$C_6$ alkoxy groups.

13. A composition comprising
(a) a thermoplastic or thermosetting resin and
(b) a compound of formula I, II, III or IV wherein $R_1$ is $C_1$–$C_{18}$ alkyl; $C_5$–$C_{12}$ cycloalkyl that is unsubstituted or substituted by one or more $C_1$–$C_6$ alkyl groups or $C_1$–$C_6$ alkoxy groups; $C_5$–$C_{22}$ aryl that is unsubstituted or substituted by one or more $C_1$–$C_6$ alkyl groups or $C_1$–$C_6$ alkoxy groups; or $C_7$–$C_{30}$ aralkyl that is unsubstituted or substituted by one or more $C_1$–$C_6$ alkyl groups or $C_1$–$C_6$ alkoxy groups and the radicals $R_2$ to $R_{13}$ are each independently of the other hydrogen: —$NO_2$; dialkylamino; alkylthio; alkylsulfonyl; halogen; $C_1$–$C_{18}$ alkyl; $C_1$–$C_{18}$ alkoxy; $C_1$–$C_{18}$ alkoxyalkyl; $C_5$–$C_{12}$ cycloalkyl that is unsubstituted or substituted by one or more $C_1$–$C_6$ alkyl groups or $C_1$–$C_6$ alkoxy groups; $C_5$–$C_{22}$ aryl that is unsubstituted or substituted by one or more $C_1$–$C_6$ alkyl groups or $C_1$–$C_6$ alkoxy groups; or $C_7$–$C_{30}$ aralkyl that is unsubstituted or substituted by one or more $C_1$–$C_6$ alkyl groups or $C_1$–$C_6$ alkoxy groups.

14. A composition according to claim 13, wherein component (b) is present in an amount from 5% to 60% by weight based on the total amount of components (a) and (b).

15. A composition according to claim 13, wherein component (b) is present in an amount from 10% to 50% by weight based on the total amount of components (a) and (b).

16. A composition according to claim 13, wherein component (b) is present in an amount from 15% to 40% by weight based on the total amount of components (a) and (b).

17. A composition according to claim 13 wherein component (a) is an epoxy resin or an oxazine resin.

18. A composition according to claim 13, wherein component (a) is an epoxy resin, component (b) optionally comprises other flame-proofing agents in addition to those recited in claim 13, and further comprising component (c) a hardener for the epoxy resin.

19. A composition according to claim 18, wherein the component (b) is present in an amount from 5% to 60% by weight based on the total amount of components (a), (b), and (c).

20. A composition according to claim 18, wherein the component (b) is present in an amount from 10% to 50% by weight based on the total amount of components (a), (b), and (c).

21. A composition according to claim 18, wherein the component (b) is present in an amount from 15% to 40% by weight based on the total amount of components (a), (b), and (c).

22. A composition according to claim 18 comprising as component (a) a diglycidyl ether of a bisphenol, an epoxy novolak, a cycloaliphatic epoxy resin or a poly(N-glycidyl) compound.

23. A composition according to claim 18 comprising as component (a) a diglycidyl ether of a bisphenol A, a diglycidyl ether of bisphenol F, an epoxyphenol novolak, an epoxycresol novalak, 3,4-epoxycyclohexylmethyl 3',4'-epoxycyclohexanecarboxylate or N,N,N',N'-tetraglycidyldiaminodiphenylmethane.

24. A composition according to claim 18, wherein the hardener is an anhydride or dicyandiamide.

25. A composition according to claim 18, wherein the hardener is tetrahydrophthalic anhydride, methyltetrahydrophthalic anhydride, hexahydrophthalic anhydride, methylhexahydrophthalic anhydride, dicyandiamide, or a novolak.

26. A composition according to claim 18, wherein the hardener is a compound of formula III or IV.

27. A cured product obtained by curing a composition according to claim 13.

* * * * *